United States Patent
Browne et al.

(10) Patent No.: US 10,527,567 B2
(45) Date of Patent: Jan. 7, 2020

(54) METHOD OF TESTING A SHAPE MEMORY ALLOY ELEMENT, AND A VALIDATION SYSTEM THEREFOR

(71) Applicant: GM GLOBAL TECHNOLOGY OPERATIONS LLC, Detroit, MI (US)

(72) Inventors: Alan L. Browne, Grosse Pointe, MI (US); Nancy L. Johnson, Northville, MI (US); Paul W. Alexander, Ypsilanti, MI (US); Geoffrey P. McKnight, Los Angeles, CA (US); Guillermo A. Herrera, Winnetka, CA (US); Christopher B. Churchill, Ventura, CA (US); Andrew C. Keefe, Encino, CA (US); Xiujie Gao, Troy, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 409 days.

(21) Appl. No.: 15/359,860

(22) Filed: Nov. 23, 2016

(65) Prior Publication Data
US 2018/0142999 A1    May 24, 2018

(51) Int. Cl.
*G01L 1/00*    (2006.01)
*G01N 25/02*    (2006.01)

(52) U.S. Cl.
CPC ................... *G01N 25/02* (2013.01)

(58) Field of Classification Search
None
See application file for complete search history.

(56) References Cited

U.S. PATENT DOCUMENTS

| 8,188,757 | B2 | 5/2012 | Herrera et al. | |
|---|---|---|---|---|
| 2009/0303839 | A1* | 12/2009 | Narayanan | G10K 9/121 367/164 |
| 2011/0163769 | A1 | 7/2011 | Herrera et al. | |
| 2012/0109573 | A1 | 5/2012 | Gao et al. | |

* cited by examiner

*Primary Examiner* — Aditya S Bhat
(74) *Attorney, Agent, or Firm* — Quinn IP Law

(57) ABSTRACT

A method of testing a SMA element includes connecting the SMA element to a validation tool, and applying an electrical current to the SMA element over a test cycle. A resistance of the SMA element during the test cycle is measured, while the electrical current is being applied. The measured resistance of the SMA element during the test cycle is correlated to an estimated strain value of the SMA element during the test cycle. A temperature of the SMA element during the test cycle is estimated. A stress in the SMA element during the test cycle is estimated from a stress predicting grid, using the estimated strain value and the estimated temperature of the SMA element during the test cycle. The proper functionality of the SMA element may be determined based on the estimated stress in the SMA element.

19 Claims, 5 Drawing Sheets

METHOD OF TESTING A SHAPE MEMORY ALLOY ELEMENT, AND A VALIDATION SYSTEM THEREFOR

TECHNICAL FIELD

The disclosure generally relates to method of testing a shape memory alloy element with a validation tool.

BACKGROUND

Shape Memory Alloy (SMA) elements may change shape in response to a control signal. For example, a SMA element may change shape when heated to a transition temperature. The SMA element may be heated, for example, with an electrical signal or current, which heats the SMA element via the inherent resistivity of the SMA element. When heated to the transition temperature, the SMA element changes from a martensite phase to an austenite phase. The change in phase is typically accompanied by a corresponding change in shape from a first shape to a second shape. When the SMA element cools to below the transition temperature, the SMA element changes from the austenite phase back to the martensite phase. The change in phase is typically accompanied by a corresponding change in shape from the second shape to the first shape.

SMA elements may be used in many different devices as an actuator and/or as a sensor. It is often necessary that the SMA element change phases at a desired transition temperature, or generate a desired force during phase transition. If the SMA element does not change phases as designed, the device may not operate as intended. It is therefore important to test SMA elements prior to installation to ensure that they are operating properly before the SMA element is installed in the device, and or test existing SMA elements already installed in a device to ensure that the SMA element is still operating as intended.

SUMMARY

A method of testing a production Shape Memory Alloy (SMA) element is provided. The method includes providing a stress predicting grid that relates stress, strain, and temperature for the production SMA element. A validation tool is connected to the production SMA element. An electrical current is applied to the production SMA element over a test cycle period. A resistance of the production SMA element during the test cycle period is measured, while the electrical current is being applied. The measured resistance of the production SMA element during the test cycle period is correlated to an estimated strain value of the production SMA element during the test cycle period. A temperature of the production SMA element during the test cycle is period is estimated. A stress in the production SMA element during the test cycle period is estimated from the stress predicting grid, using the estimated strain value and the estimated temperature of the production SMA element during the test cycle period. The proper functionality of the production SMA element may be determined based on the estimated stress in the production SMA element.

A validation tool for testing a Shape Memory Alloy (SMA) element is also provided. The validation tool includes a resistance sensor for sensing a resistance of the SMA element, and a data acquisition unit in communication with the resistance sensor. A tool controller is in communication with the data acquisition unit. The tool controller includes a processor and non-transitory memory on which is recorded a test algorithm. The processor is operable to execute the test algorithm to perform the following functions. Specifically, the test algorithm is executed to apply an electrical current to the SMA element for a test cycle, and measure a resistance in the SMA element during the test cycle. The tool controller estimates a strain in the SMA element, based on the measured resistance in the SMA element during the test cycle. The tool controller estimates a temperature of the SMA element during the test cycle. The tool controller estimates stress in the SMA element during the test cycle, with a stress predicting grid, which correlates the estimated strain in the SMA element during the test cycle and the estimated temperature of the SMA element during the test cycle, to the estimated stress in the SMA element during the test cycle.

A calibration rig for use with a calibration tool is also provided. The calibration rig includes a force generator that is configured for attachment to a first axial end of the SMA element. The force generator is operable to apply a predetermined force to the SMA element. A load cell is configured for attachment to a second axial end of the SMA element. The load cell is operable to sense the force applied to the SMA element. A measuring device is configured to measure an axial displacement of the SMA element along an axis.

The calibration rig is used in conjunction with the calibration tool to develop the stress predicting grid and a resistance-strain table, which are stored in the memory of the tool controller. The tool controller may then be attached to the production SMA element, and by sensing only the resistance in the production SMA element during a transformation cycle of the SMA element, may estimate the stress in the production SMA element. The production SMA element may be tested pre-installation to determine proper functionality prior to manufacture, or may be tested post-installation to determine proper functionality after the production SMA element has been installed in a final product, such as an automobile.

The above features and advantages and other features and advantages of the present teachings are readily apparent from the following detailed description of the best modes for carrying out the teachings when taken in connection with the accompanying drawings.

DETAILED DESCRIPTION

Those having ordinary skill in the art will recognize that terms such as "above," "below," "upward," "downward," "top," "bottom," etc., are used descriptively for the figures, and do not represent limitations on the scope of the disclosure, as defined by the appended claims. Furthermore, the teachings may be described herein in terms of functional and/or logical block components and/or various processing steps. It should be realized that such block components may be comprised of any number of hardware, software, and/or firmware components configured to perform the specified functions.

Figure 1:
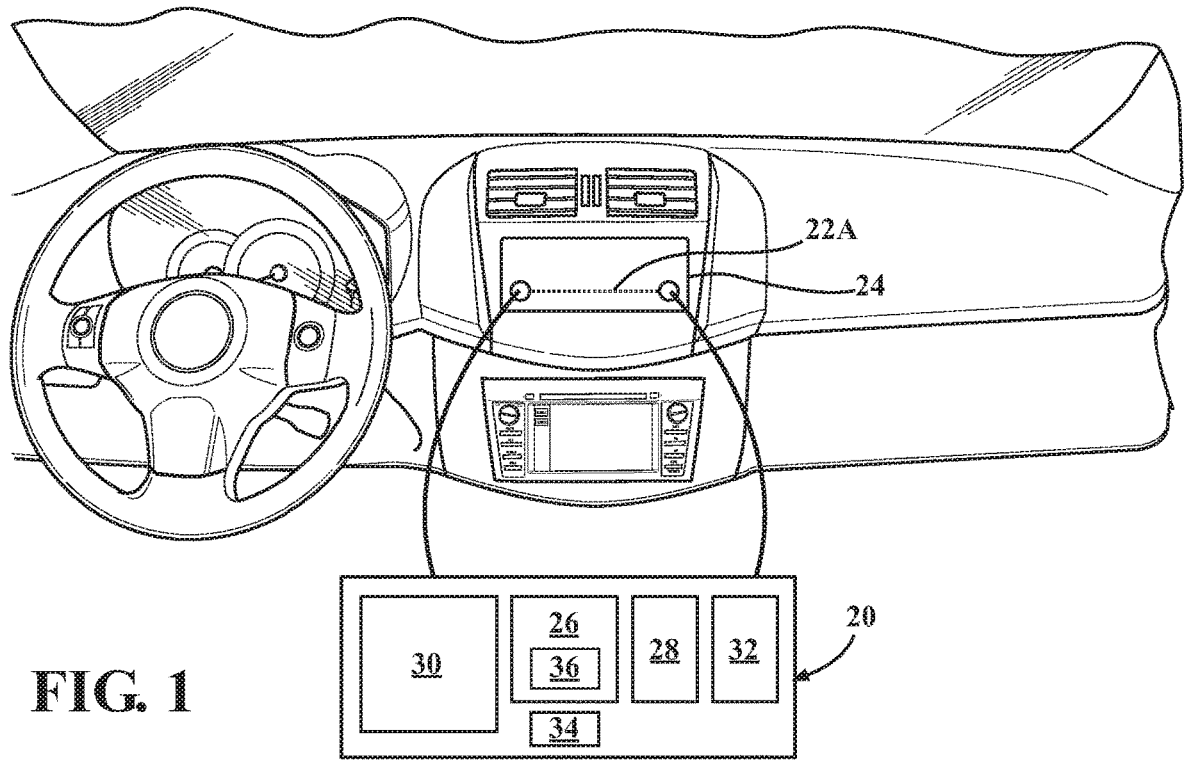
FIG. 1 is a schematic plan of a validation tool connected to a Shape Memory Alloy (SMA) device, for testing a production SMA element.
Figure 2:
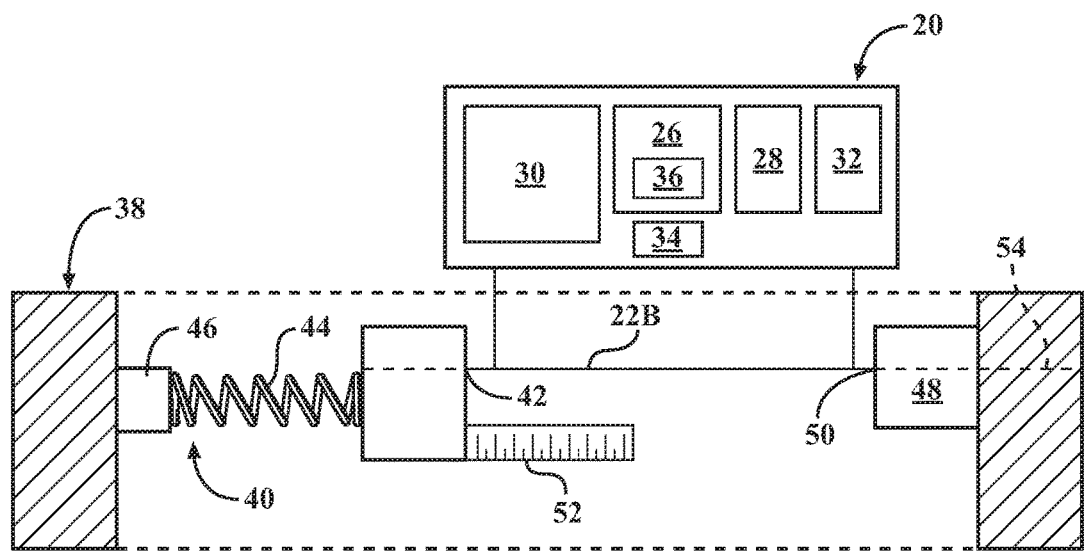
FIG. 2 is a schematic plan view of the validation tool connected to a sample SMA element in a calibration rig for calibrating the validation tool.

Referring to the Figures, wherein like numerals indicate like parts throughout the several views, a validation tool is generally shown at 20 in FIG. 1. The validation tool 20 may be used to test a Shape Memory Alloy (SMA) element. The SMA element may include, but is not limited to, a production SMA element 22A, such as shown in FIG. 1, or a sample SMA element 22B, such as shown in FIG. 2. The production SMA element 22A and the sample SMA element 22B are referred to generically within the written description by the reference numeral 22, whereas the production SMA element 22A is referred to specifically and shown in the Figures by the reference numeral 22A, and the sample SMA element 22B is referred to specifically and shown in the Figures by the reference numeral 22B. As used herein, the production SMA element 22A may include an SMA element 22 that has been produced and is intended for use in a SMA device 24. The production SMA element 22A may be tested prior to installation in the SMA device 24, to determine proper functionality prior to manufacture, or after installation in the SMA device 24 to diagnose proper functionality after installation. As used herein, the sample SMA element 22B is used during a calibration process to develop the requisite data tables necessary to test the production SMA element 22A. It should be appreciated that the production SMA element 22A and the sample SMA element 22B are preferably identical, and are only identified differently herein to help differentiate between a calibration process and a testing process. However, the production SMA element 22A and the sample SMA element 22B may have different geometries, and therefore need not be identical. However, the production SMA element 22A and the sample SMA element 22B should be of the same material, i.e., alloy. The accuracy of the process is reduced when the production SMA element 22A and the sample SMA element 22B are not identical.

The SMA element 22 is manufactured from a shape memory alloy. Suitable shape memory alloys can exhibit a one-way shape memory effect, an intrinsic two-way effect, or an extrinsic two-way shape memory effect depending on the alloy composition and processing history. The two phases that occur in shape memory alloys are often referred to as martensite and austenite phases. The martensite phase is a relatively soft and easily deformable phase of the shape memory alloys, which generally exists at lower temperatures. The austenite phase, the stronger phase of shape memory alloys, occurs at higher temperatures. Shape memory materials formed from shape memory alloy compositions that exhibit one-way shape memory effects do not automatically reform, and depending on the shape memory material design, will likely require an external mechanical force to reform the shape orientation that was previously exhibited. Shape memory materials that exhibit an intrinsic shape memory effect are fabricated from a shape memory alloy composition that will automatically reform themselves.

The temperature at which the shape memory alloy remembers its high temperature form when heated can be adjusted by slight changes in the composition of the alloy and through heat treatment. In nickel-titanium shape memory alloys, for example, it can be changed from above about 100° C. to below about −100° C. The shape recovery process occurs over a range of just a few degrees and the start or finish of the transformation can be controlled to within a degree or two depending on the desired application and alloy composition. The mechanical properties of the shape memory alloy vary greatly over the temperature range spanning their transformation, typically providing the shape memory material with shape memory effects as well as high damping capacity. The inherent high damping capacity of the shape memory alloys can be used to further increase the energy absorbing properties.

Suitable shape memory alloy materials include without limitation nickel-titanium based alloys, indium-titanium based alloys, nickel-aluminum based alloys, nickel-gallium based alloys, copper based alloys (e.g., copper-zinc alloys, copper-aluminum alloys, copper-gold, and copper-tin alloys), gold-cadmium based alloys, silver-cadmium based alloys, indium-cadmium based alloys, manganese-copper based alloys, iron-platinum based alloys, iron-platinum based alloys, iron-palladium based alloys, and the like. The alloys can be binary, ternary, or any higher order so long as the alloy composition exhibits a shape memory effect, e.g., change in shape orientation, damping capacity, and the like. For example, a nickel-titanium based alloy is commercially available under the trademark NITINOL from Shape Memory Applications, Inc.

The shape memory alloy, may be activated with an activation signal using any suitable means, preferably a means for subjecting the material to a temperature change above, or below, a transition temperature. For example, for elevated temperatures, heat may be supplied using hot gas (e.g., air), steam, hot liquid, or electrical current. The activation means may, for example, be in the form of heat conduction from a heated element in contact with the shape memory material, heat convection from a heated conduit in proximity to the thermally active shape memory material, a hot air blower or jet, microwave interaction, resistive heating, and the like. In the case of a temperature drop, heat may be extracted by using cold gas, or evaporation of a refrigerant. The activation means may, for example, be in the form of a cool room or enclosure, a cooling probe having a cooled tip, a control signal to a thermoelectric unit, a cold air blower or jet, or means for introducing a refrigerant (such as liquid nitrogen) to at least the vicinity of the shape memory material.

The activation signal, which is provided by an activation device, may include a heat signal, a magnetic signal, an electrical signal, a pneumatic signal, a mechanical signal, and the like, and combinations comprising at least one of the foregoing signals, with the particular activation signal dependent on the materials and/or configuration of the active material. For example, a heat signal or an electrical signal may be applied for changing the property of the shape memory alloy.

Referring to FIG. 1, the validation tool 20 includes a data acquisition unit 26, a resistance sensor 28, a power supply 34, and a tool controller 30. In addition, the validation tool 20 may further include a thermocouple 32. The data acquisition unit 26 is disposed in communication with the resistance sensor 28 and the thermocouple 32 for communicating and receiving data from the resistance sensor 28 and the thermocouple 32. The data acquisition unit 26 may include any unit or device that has sufficient resolution to record or measure a 0.1% change in the resistance of the SMA element 22, a 0.02% change in length of the SMA element 22, a 1.0° C. change in ambient temperature, and a 1.0% change in force. In practice, a properly ranged 16-bit data acquisition unit 26 may work well. However, if the range of expected wire geometries is reduced, the data acquisition unit 26 could be as low as a 12-bit unit.

The resistance sensor 28 is operable to sense the resistance of the SMA element 22. The resistance sensor 28 may include any suitable type of sensor that is capable of sensing resistance in a wire. Preferably, and as shown in the Figures, the resistance sensor 28 includes a four point sensing unit and a current-sensing shunt. As is known to those skilled in the art, current is sent through both a current-sensing shunt (i.e., current sensor 36) and the SMA element 22 through a circuit A, and the voltage drop across the SMA element 22 is measured with a separate pair of wires, using a circuit B (not shown), so as to account for leadwire resistance in a circuit A (not shown). The current in circuit A may be measured by a shunt resistor, hall-effect resistor, or any other current sensor 36. Separating circuit A from circuit B eliminates the lead and contact resistance from the resistance measurement, which provides a more precise measurement of the resistance. Alternatively, the resistance sensor 28 may include a two point sensing unit. However, if the resistance sensor 28 includes a two point sensing unit, the resistance in the leads must be accounted for. For example, the resistance of the leadwires may be estimated by their length and gauge.

The validation tool 20 may further include the thermocouple 32. However, it should be appreciated that the validation tool 20 is not required to include the thermocouple 32. The thermocouple 32 is disposed in communication with the data acquisition unit 26 for transmitting data thereto. The thermocouple 32 is operable to sense an ambient air temperature adjacent the SMA element 22. The thermocouple 32 may include any type of sensor that is capable of sensing or otherwise determining the ambient air temperature adjacent the SMA element 22.

While only two wires are depicted in FIG. 1 connecting the validation tool 20 to the production SMA element 22A in the SMA device 24, it should be appreciated that this is merely a schematic representation, and that the validation tool 20 may include any number of wires needed to connect the validation tool 20 to the production SMA device 24 in order to collect the required data for the data acquisition unit 26.

The tool controller 30 is disposed in communication with the data acquisition unit 26. The tool controller 30 may include and/or be referred to as a controller, a control module, a computer, etc. The tool controller 30 is operable to control the operation of the validation tool 20. The tool controller 30 may include a computer and/or processor, and include all software, hardware, memory, algorithms, connections, sensors, etc., necessary to manage and control the operation of the validation tool 20. As such, a method of testing the SMA device 24 may be at least partially embodied as a program operable on the tool controller 30. It should be appreciated that the tool controller 30 may include any device capable of analyzing data from various sensors, comparing data, making the necessary decisions required to control the operation of the validation tool 20, and executing the required tasks necessary to control the operation of the validation tool 20.

The tool controller 30 may be embodied as one or multiple digital computers or host machines each having one or more processors, read only memory (ROM), random access memory (RAM), electrically-programmable read only memory (EPROM), optical drives, magnetic drives, etc., a high-speed clock, analog-to-digital (A/D) circuitry, digital-to-analog (D/A) circuitry, and any required input/output (I/O) circuitry, I/O devices, and communication interfaces, as well as signal conditioning and buffer electronics.

The computer-readable memory may include any non-transitory/tangible medium which participates in providing data or computer-readable instructions. Memory may be non-volatile or volatile. Non-volatile media may include, for example, optical or magnetic disks and other persistent memory. Example volatile media may include dynamic random access memory (DRAM), which may constitute a main memory. Other examples of embodiments for memory include a floppy, flexible disk, or hard disk, magnetic tape or other magnetic medium, a CD-ROM, DVD, and/or any other optical medium, as well as other possible memory devices such as flash memory.

The tool controller 30 includes tangible, non-transitory memory on which are recorded computer-executable instructions, including a test algorithm. The processor of the controller is configured for executing the test algorithm. The test algorithm implements a method of testing the SMA device 24, described in greater detail below.

Prior to the validation tool 20 being used to test the production SMA element 22A, various data files must be created and saved in the memory of the tool controller 30. Specifically, a relationship between resistance, strain, and temperature for the SMA element 22 and a stress predicting grid 31 or map must be defined and saved into the memory of the tool controller 30. In order to generate these files, a calibration rig 38 may be used in combination with the validation tool 20, to generate the data necessary to create these files.

Referring to FIG. 2, the validation tool 20 is shown attached to the sample SMA element 22B in the calibration rig 38. While only two wires are depicted in FIG. 2 connecting the validation tool 20 to the sample SMA element 22B in the calibration rig 38, it should be appreciated that this is merely a schematic representation, and that the validation tool 20 may include any number of wires needed to connect the validation tool 20 to the sample SMA element 22B in order to collect the required data for the data acquisition unit 26.

Referring to FIG. 2, the calibration rig 38 includes a force generator 40 that is configured for attachment to a first axial end 42 of the sample SMA element 22B. The force generator 40 is operable to apply a pre-determined force to the SMA element 22. The force generator 40 may include any device or combination of mechanisms that is capable of providing a controllable, consistent and uniform force to the sample SMA element 22B throughout the stroke or displacement of the SMA element 22 that occurs during a phase transformation. For example, the force generator 40 may include, a very long spring, referred to hereinafter as a constant force spring 44, which is approximately four times longer than the SMA element 22. The constant force spring 44 is coupled to a stepper motor 46, which is operable to change the amount of tension in the constant force spring 44. The length of the constant force spring 44 is sufficient so that the small displacement of the SMA element 22 (typically 5 mm in most common SMA elements 22 for example), would not change the tension in the constant force spring 44 by more than 10% throughout the stroke or displacement of the sample SMA element 22B during the phase transformation. The stepper motor 46 may be configured to move an end of the constant force spring 44 (approximately 100 mm for most common SMA elements 22, for example) when different loads are required. It should be appreciated that the force generator 40 may include some other device not specifically described or shown herein, that is capable of applying and maintaining a constant load to the sample SMA element 22B during its phase transformation.

The calibration rig 38 further includes a load cell 48. The load cell 48 is configured for attachment to a second axial end 50 of the sample SMA element 22B. The load cell 48 is operable to sense and monitor the force applied to the sample SMA element 22B. The load cell 48 may include any suitable sensor that is capable of sensing the tensile force in the sample SMA element 22B throughout the phase transformation of the sample SMA element 22B. For example, the load cell 48 may include, but is not limited to, a strain gauge with a Wheatstone bridge. Preferably, the load cell 48 is capable of sensing a 1.0% change in load from the nominal operating stress of the SMA element 22.

The calibration rig 38 further includes a measuring device 52. The measuring device 52 is operable to measure an axial displacement of the sample SMA element 22B along an axis 54 of the sample SMA element 22B. For example, during phase transformation of the sample SMA element 22B, the axial length of the sample SMA element 22B may change, thereby generating a stroke or displacement distance. The displacement distance may be considered the change in axial length along the axis 54 of the sample SMA element 22B that occurs during phase transformation. The measuring device 52 may include any device that is capable of measuring the displacement distance. The measuring device 52 may include, but is not limited to, a ruler, tape measure, optical scanner, laser distance sensor, or some other device that may be used to measure the displacement distance. Preferably, the measuring device 52 is capable of measuring or sensing a 0.02% change in the length of the SMA element 22.

As noted above, the calibration rig 38 and the validation tool 20 may be used to generate the necessary data that is required to develop or provide the stress predicting grid 31. The stress predicting grid 31 correlates stress, strain, and temperature for the SMA element 22. Accordingly, given any two of the stress, strain, and temperature, the stress predicting grid 31 may be used to determine the remaining one of the stress, strain, and temperature. For example, for given strain and temperature values of the SMA element 22, the stress may be determined by referencing the stress predicting grid 31.

The sample SMA element 22B is tested in the calibration rig 38 to generate the data that is necessary to generate the relationship between strain, resistance, and temperature, as well as the stress predicting grid 31. The calibration rig 38 is operable to apply a pre-determined force to the sample SMA element 22B, while the validation tool 20 applies a current to the sample SMA element 22B and measures the resultant resistance in the sample SMA element 22B, during a calibration cycle period. The calibration cycle period is the length of time that the pre-determined force and the current are applied to the sample SMA element 22B. The measuring device 52 is used to measure the resulting displacement of the sample SMA element 22B during the calibration cycle period, which occurs as a result of phase transformation of the sample SMA element 22B. It should be appreciated that the initial length, cross sectional area, and specific material of the sample SMA element 22B are known prior to testing the sample SMA element 22B. The sample SMA element 22B should be identical to, or at least similar to, the production SMA element 22A that is intended to be tested by the validation tool 20.

The sample SMA element 22B is tested multiple times, with each of the multiple tests using a different pre-determined force. For example, the force generator 40 may be controlled to apply 100 MPA force to the sample SMA element 22B, while the validation tool 20 applies a constant heating current to the sample SMA element 22B to heat the sample SMA element 22B to or above its transformation temperature. Upon reaching the transformation temperature, the sample SMA element 22B changes phases, which may result in axial displacement along the axis 54 of the sample SMA element 22B. The displacement distance may be obtained from the measuring device 52. The load cell 48 measures the tensile force in the sample SMA element 22B. The measurements data obtained from or related to the sample SMA test include the force applied to the sample SMA element 22B, e.g., the 100 MPA pre-determined force, the displacement distance, the current that was applied to the sample SMA element 22B, and the resistance in the sample SMA element 22B. The test may be repeated at different pre-determined forces. For example, in addition to testing the sample SMA element 22B at 100 MPA, such as described above, the sample SMA element 22B may be tested with a pre-determined force of 200 MPA, 300 MPA, and 400 MPA, with each test at each pre-determined force providing the various measurements described above.

Figure 3:
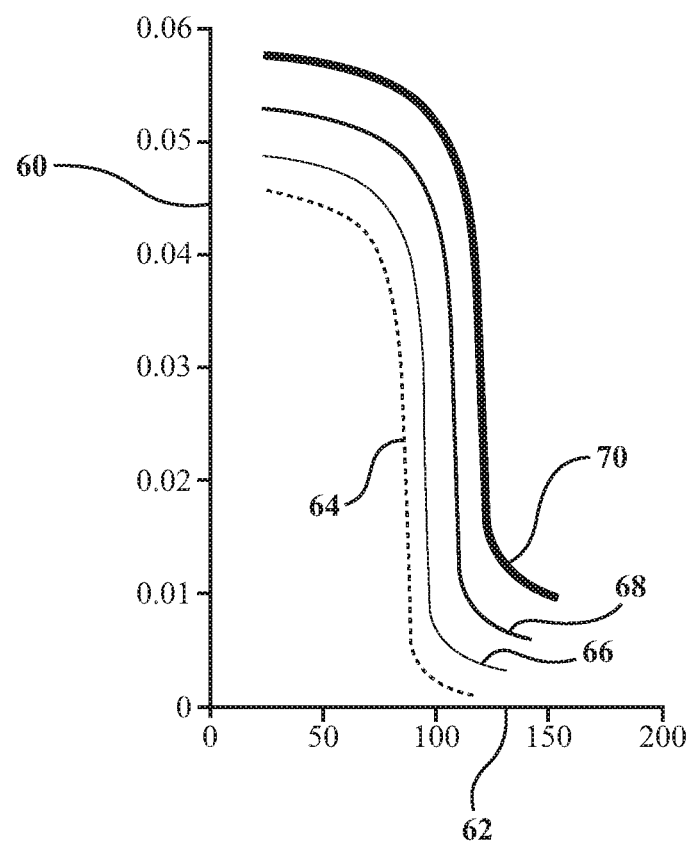
FIG. 3 is a graph showing strain vs. temperature of the sample SMA element for multiple calibration test cycles at varying applied forces.

An engineering strain in the sample SMA element 22B may also calculated during the calibration cycle period, for each of the different pre-determined loads. The engineering strain may be calculated from the measured displacement of the sample SMA element 22B during the calibration cycle period. For example, the engineering strain may be calculated by dividing the measured displacement of the sample SMA element 22B by the length of the SMA element 22 prior to phase transformation, i.e., the original length of the sample SMA element 22B. Referring to FIG. 3, the calculated engineering strain in the sample SMA element 22B, for each of four different tests of the sample SMA element 22B at four different pre-determined forces are shown. As shown in FIG. 3, strain is shown along a vertical axis 60, and an estimated temperature of the sample SMA element 22B in degrees Celsius is shown along a horizontal axis 62. The strain in the sample SMA element 22B with an applied pre-determined force of 100 MPA is shown by reference line 64. The strain in the sample SMA element 22B with an applied pre-determined force of 200 MPA is shown by reference line 66. The strain in the sample SMA element 22B with an applied pre-determined force of 300 MPA is shown by reference line 68. The strain in the sample SMA element 22B with an applied pre-determined force of 400 MPA is shown by reference line 70.

The temperature of the sample SMA element 22B during the calibration test cycle is estimated by a heat transfer model. Preferably, a lumped sum heat transfer model is used to estimate the temperature of the sample SMA element 22B throughout the calibration test cycle for each of the different tests at the different applied loads. As is known in the art, the heat transfer model estimates heat input to the SMA element 22 (i.e., resistive heating), heat stored in the SMA element 22 (i.e., specific heat), heat converted to phase transformation (i.e., latent heat of transformation), and heat lost to the environment (i.e., convective cooling). By accurately measuring and modeling all of these heat inputs and outputs, the temperature of the SMA element 22 may be estimated.

Testing the sample SMA element 22B provides the current that is applied to the sample SMA element 22B and the resulting voltage in the SMA element 22 during the calibration cycle period. The current and voltage may then be used to calculate the resistance of the sample SMA element 22B during the calibration cycle period. The resistance may be calculated by dividing the voltage by the current. The resistance is calculated for each test of the sample SMA element 22B, throughout the calibration cycle period, for each of the different pre-determined loads. The calculated resistance in the sample SMA element 22B during the calibration cycle period, for each test at the different applied loads, may then be used to calculate a resistivity of the sample SMA element 22B during the calibration cycle period, for each test at the different applied loads. The resistivity of the sample SMA element 22B may be calculated by multiplying the resistance of the sample SMA element 22 by the cross sectional area of the sample SMA element 22B, and then dividing that product by the original length of the sample SMA element 22B, i.e., the length of the sample SMA element 22B prior to phase transformation.

Figure 4:
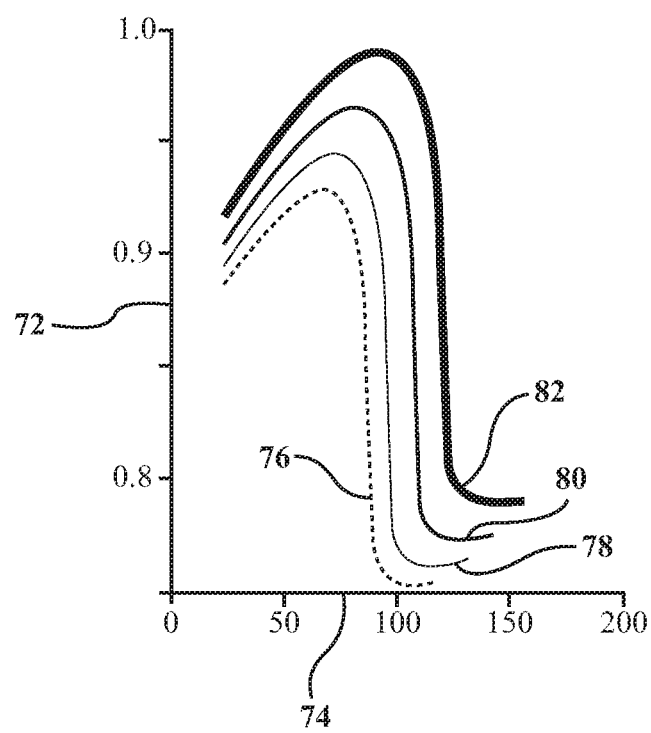
FIG. 4 is a graph showing resistivity vs. temperature of the sample SMA element during the multiple calibration test cycles at the varying applied forces.

Referring to FIG. 4, the calculated resistivity in the sample SMA element 22B, for each of four different tests of the sample SMA element 22B at four different pre-determined forces are shown. As shown in FIG. 4, resistivity in micro ohm-meters is shown along a vertical axis 72, and an estimated temperature of the sample SMA element 22B in degrees Celsius is shown along a horizontal axis 74. The resistivity in the sample SMA element 22B with an applied pre-determined force of 100 MPA is shown by reference line 76. The resistivity in the sample SMA element 22B with an applied pre-determined force of 200 MPA is shown by reference line 78. The resistivity in the sample SMA element 22B with an applied pre-determined force of 300 MPA is shown by reference line 80. The resistivity in the sample SMA element 22B with an applied pre-determined force of 400 MPA is shown by reference line 82.

In addition to the above described measurements that are obtained during the different tests of the sample SMA element 22B, the validation tool 20 may further measure the ambient air temperature adjacent the sample SMA element 22B, during the calibration cycle period. The ambient air temperature may be used to correct or adjust the estimated temperature of the sample SMA element 22B for ambient conditions.

An optimization tool may use the collected data, generally represented by the graphs shown in FIGS. 3 and 4, to generate five constants, which optimally describe the relationship between resistivity, strain, and temperature in the sample SMA element 22B, maximizing the accuracy of the validation tool 20. The relationship between resistivity, strain, and temperature are defined by Equations 1 and 2, described in greater detail below.

Figure 5:
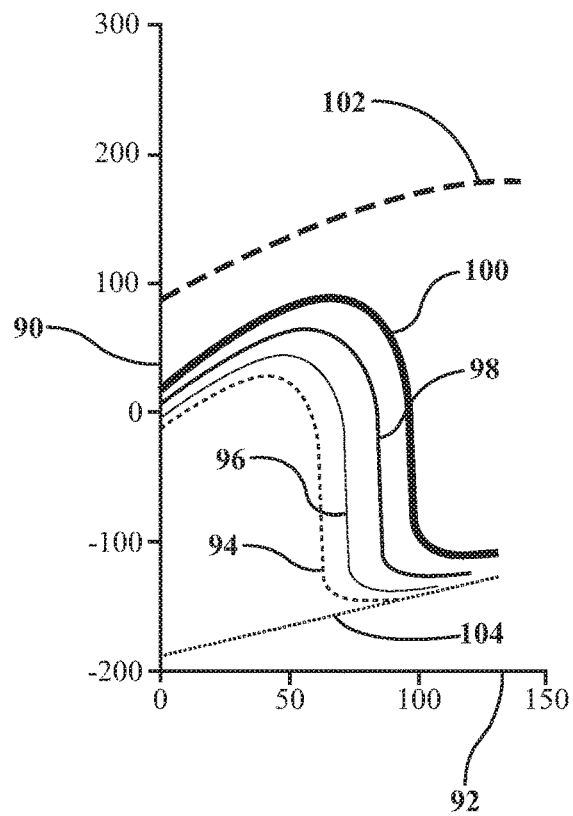
FIG. 5 is a graph showing adjusted resistivity vs. temperature of the sample SMA element during the multiple calibration test cycles at the varying applied forces.

Referring to FIG. 5, a normalized resistivity of the sample SMA element 22B vs. an adjusted temperature of the sample SMA element 22B for the different force tests are generally shown. The normalized resistivity is shown along a vertical axis 90, and the adjusted temperature of the sample SMA element 22B in degrees Celsius is shown along a horizontal axis 92. The normalized resistivity is the numeric difference between the resistivity of the sample SMA element 22B (shown in FIG. 4) and a reference resistivity value, then divided by some normalizing resistivity. The reference resistivity value may include any value, including zero. The reference resistivity adds stability to the optimization algorithm by reducing round-off errors. The adjusted temperature of the SMA element 22 is the numerical difference between the estimated temperature of the sample SMA element 22B, derived from the heat transfer model, and the sensed ambient air temperature adjacent the sample SMA element 22B.

Referring to FIG. 5, the normalized resistivity in the sample SMA element 22B, for each of four different tests of the sample SMA element 22B at four different pre-determined forces are shown. As shown in FIG. 5, the adjusted resistivity in the sample SMA element 22B with an applied pre-determined force of 100 MPA is shown by reference line 94. The adjusted resistivity in the sample SMA element 22B with an applied pre-determined force of 200 MPA is shown by reference line 96. The adjusted resistivity in the sample SMA element 22B with an applied pre-determined force of 300 MPA is shown by reference line 98. The adjusted resistivity in the sample SMA element 22B with an applied pre-determined force of 400 MPA is shown by reference line 100. The relationship between resistance and temperature for pure martensite for the sample SMA element 22B is shown by reference line 102. The relationship between resistance and temperature for pure austenite for the sample SMA element 22B is shown by reference line 104.

The resistivity of the sample SMA element 22B in pure martensite form may be calculated using the quadratic Equation 1 below.

$$\rho = \xi(\alpha_{M1}T + \alpha_{M2}T^2 + \lambda_M) + (1-\xi)(\alpha_A T + \lambda_M) \qquad 1)$$

Referring to Equation 1 above, $\rho$ is the resistivity of the sample SMA element 22B, $\xi$ is the martensite phase fraction of the sample SMA element 22B, $\alpha_{M1}$ is the linear portion of the slope of the line 102 relating resistance and temperature for pure martensite of the sample SMA element 22B, $\alpha_{M2}$ is quadratic portion of the line 102 relating resistance and temperature for pure martensite of the sample SMA element 22B, T is the estimated temperature of the sample SMA element 22B, $\lambda_M$ is the resistance offset of pure martensite at a reference temperature, and $\alpha_A$ is the slope of the line 104 relating resistance and temperature for pure austenite of the sample SMA element 22B.

The martensite phase fraction of the sample SMA element 22B may be calculated from Equation 2 below.

$$\xi = \frac{\varepsilon - \frac{\sigma}{E}}{\beta} \qquad 2)$$

Referring to Equation 2 above, $\xi$ is the martensite phase fraction of the sample SMA element 22B, $\varepsilon$ is the total material strain in the sample SMA element 22B, $\sigma$ is the stress in the sample SMA element 22B, E is the elastic modulus in the sample SMA element 22B, and $\beta$ is the stress free transformation strain in the sample SMA element 22B. $\beta$ may be defined as the total strain in the sample SMA element 22B when the phase fraction is fully martensite (i.e., $\xi=1$) and there is no stress (i.e., $\sigma=0$).

The resistivity of the sample SMA element 22B in pure austenite form may be calculated using the quadratic Equation 1 above, with the martensite phase fraction $\xi$ equal to zero.

Figure 6:
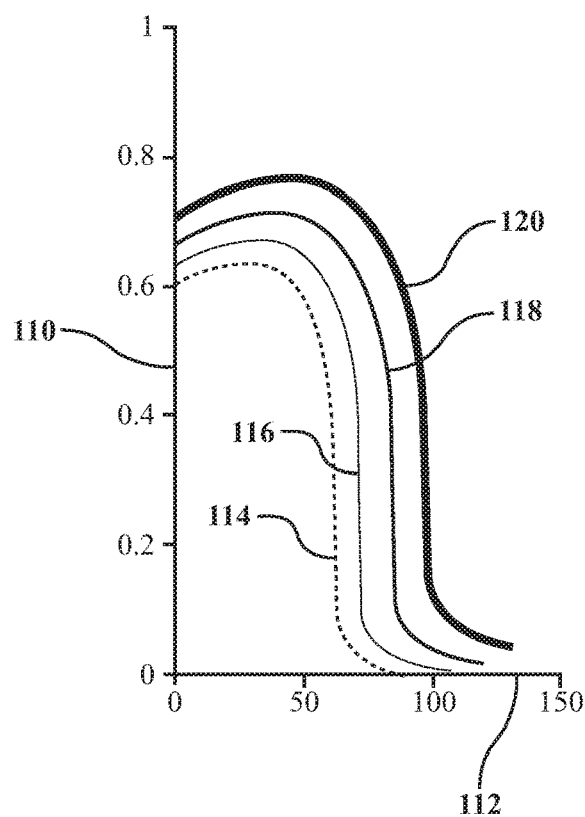
FIG. 6 is a graph showing a martensite phase fraction vs. temperature of the sample SMA element during the multiple calibration test cycles at the varying applied forces.

Referring to FIG. 6, the martensite phase fraction in the sample SMA element 22B, for each of four different tests of the sample SMA element 22B at four different pre-determined forces are shown. As shown in FIG. 6, martensite phase fraction in percent phase transformation is shown along a vertical axis 110, and the adjusted temperature of the sample SMA element 22B in degrees Celsius is shown along a horizontal axis 112. As noted above, the adjusted temperature of the SMA element 22 is the numerical difference between the estimated temperature of the sample SMA element 22B, derived from the heat transfer model, and the sensed ambient air temperature adjacent the sample SMA element 22B. The martensite phase fraction in the sample SMA element 22B with an applied pre-determined force of 100 MPA is shown by reference line 114. The martensite phase fraction in the sample SMA element 22B with an applied pre-determined force of 200 MPA is shown by reference line 116. The martensite phase fraction in the sample SMA element 22B with an applied pre-determined force of 300 MPA is shown by reference line 118. The martensite phase fraction in the sample SMA element 22B with an applied pre-determined force of 400 MPA is shown by reference line 120.

Figure 7:
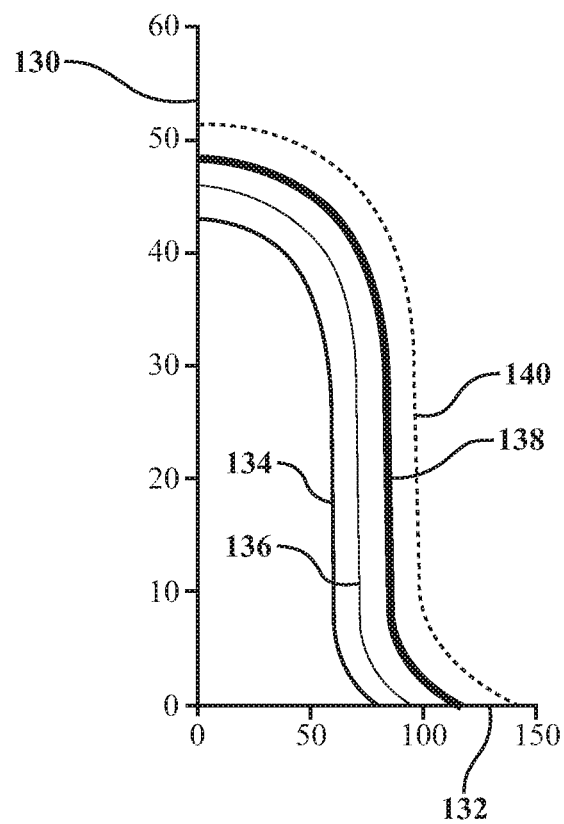
FIG. 7 is a graph showing strain vs. temperature of the sample SMA element during the multiple calibration test cycles at the varying applied forces.

Referring to FIG. 7, the transformation strain in the sample SMA element 22B, for each of four different tests of the sample SMA element 22B at four different pre-determined forces is shown. The transformation strain is equal to the martensite phase fraction $\xi$ multiplied by the stress free transformation strain $\beta$, and is also equal to the total material strain $\varepsilon$ in the sample SMA element 22B minus the elastic strain in the sample SMA element 22B. The elastic strain may be calculated by dividing the stress in the sample SMA element 22B $\sigma$ by the engineering strain in the sample SMA element 22B (i.e., deflection divided by length).

As shown in FIG. 7, the transformation strain in milli units is shown along a vertical axis 130, and the adjusted temperature of the sample SMA element 22B in degrees Celsius is shown along a horizontal axis 132. As noted above, the adjusted temperature of the SMA element 22 is the numerical difference between the estimated temperature of the sample SMA element 22B, derived from the heat transfer model, and the sensed ambient air temperature adjacent the sample SMA element 22B. The transformation strain in the sample SMA element 22B with an applied pre-determined force of 100 MPA is shown by reference line 134. The transformation strain in the sample SMA element 22B with an applied pre-determined force of 200 MPA is shown by reference line 136. The transformation strain in the sample SMA element 22B with an applied pre-determined force of 300 MPA is shown by reference line 138. The transformation strain in the sample SMA element 22B with an applied pre-determined force of 400 MPA is shown by reference line 140.

That data generally represented by the graphs shown in FIGS. 3 and 4, may also be used to develop or generate the stress predicting grid 31. As noted above, the stress predicting grid 31 correlates strain, stress, and temperature of the sample SMA element 22B.

The stress in the sample SMA element 22B during the calibration cycle period may be calculated from the predetermined force applied to the sample SMA element 22B during the calibration cycle period. Specifically, the stress in the sample SMA element 22B is equal to the pre-defined force divided by the cross sectional area of the sample SMA element 22B. Accordingly, the stress predicting grid 31 may be provided from the calculated strain in the sample SMA element 22B, the calculated stress in the sample SMA element 22B, and the estimated temperature of the sample SMA element 22B.

Figure 8:
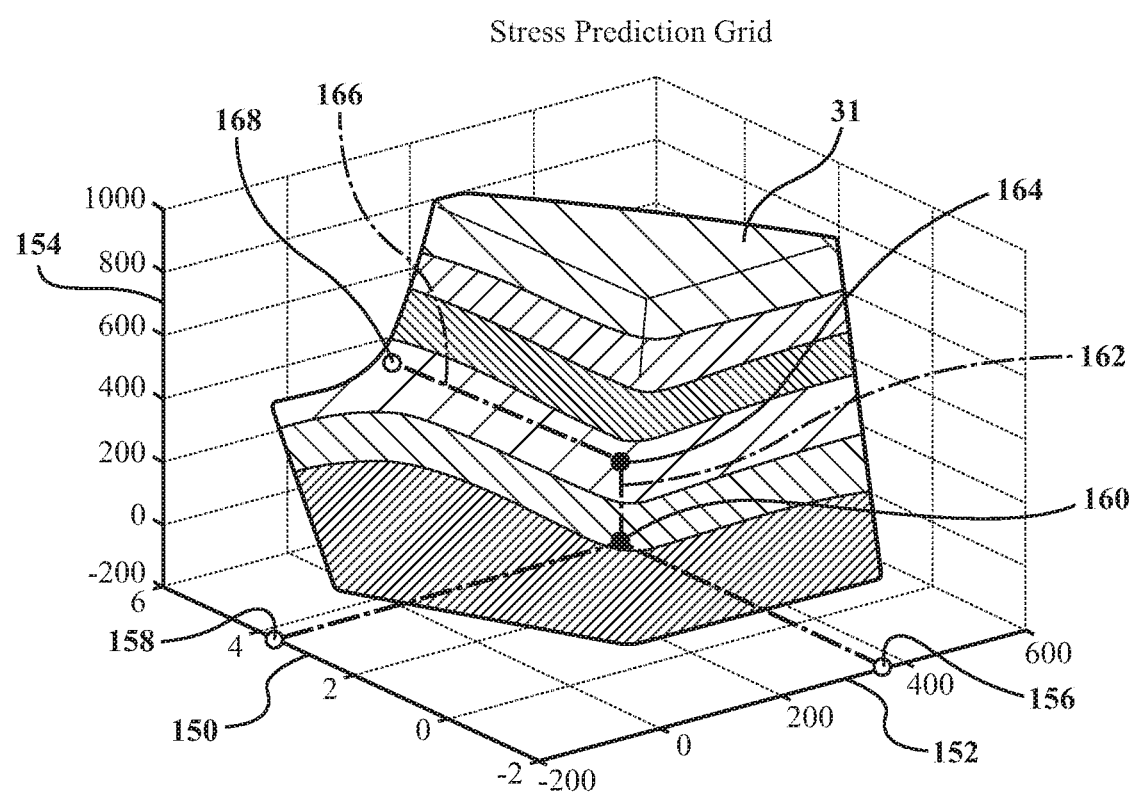
FIG. 8 is a graph representing a stress predicting grid showing the relationship between stress, strain and temperature for the sample SMA element during the multiple calibration test cycles at the varying applied forces.

Referring to FIG. 8, the stress predicting grid 31 is represented as a three dimensional graph. As shown in FIG. 8, the strain in percent of the sample SMA element 22B is shown along a first horizontal axis 150, the estimated temperature of the sample SMA element 22B in degrees Celsius is shown along a second horizontal axis 152, and the stress in the sample SMA in mega pascal (MPa) is shown along a vertical axis 154. The hatched three dimensional region, i.e., the stress predicting grid, generally shown at 31 represents the valid states of the sample SMA element 22B during heating.

Once the relationship between resistivity, strain, and temperature have been developed from Equations 1 and 2 above and the stress predicting grid 31 has been generated and/or defined, using the sample SMA element 22B, they may be saved in the memory of the tool controller 30, and used to test the production SMA element 22A. As noted above, the sample SMA element 22B and the production SMA element 22A are preferably identical, or at least similar in cross sectional area, length, and material. It should be appreciated that differences between the production SMA element 22A and the sample SMA element 22B will introduce variability into the test results.

Referring to FIG. 1, the method of testing the production SMA element 22A, includes connecting the validation tool 20 to the production SMA element 22A. Specifically, the probes of the resistance sensor 28 are attached to the production SMA element 22A. If the production SMA element 22A is being tested in a factory, prior to installation in the SMA device 24, then the validation tool 20 may be simply clamped onto or otherwise affixed to the production SMA element 22A. However, if the production SMA element 22A is being tested after installation or manufacture of the SMA device 24, then it may be necessary to provide access terminals or ports for connecting the probes of the resistance sensor 28 to the production SMA element 22A.

Once the resistance sensor 28 is connected to the production SMA element 22A, the tool controller 30 may sense or measure the resistance in the production SMA element 22A during phase transformation of the production SMA element 22A. Sensing the resistance in the production SMA element 22A may include applying a constant electrical current to the production SMA element 22A over a test cycle period, and measuring the resulting voltage through the production SMA element 22A during the test cycle period. The test cycle period is the period of time required to heat the production SMA element 22A to its transformation temperature and for the production SMA element 22A to complete its phase transformation. As described above and known in the art, the resistance of the production SMA element 22A may be calculated by dividing the measured voltage through the production SMA element 22A by the measured current applied to the production SMA element 22A.

Using the measured (or calculated) resistance from the production SMA element 22A, the strain in the production SMA element 22A may be estimated by using the relationship between resistance, strain, and temperature, that were developed using Equations 1 and 2 above. As described above, Equations 1 and 2 above correlate the measured resistance of the production SMA element 22A during the test cycle period to the estimated strain of the production SMA element 22A during the test cycle period, for different temperatures of the production SMA element 22A during the test cycle period.

The temperature of the production SMA element 22A is also estimated during the test cycle period. As described above during the calibration process, the tool controller 30 may estimate the temperature of the production SMA element 22A using a heat transfer model, which estimates the heat of the production SMA element 22A during the test cycle period based on the amount of energy input into the production SMA element 22A, i.e., the amount and duration that the current is applied to the production SMA element 22A during the test cycle period.

The tool controller 30 may then estimate the stress in the production SMA element 22A during the test cycle period, by using the stress predicting grid 31, based on the estimated strain value, and the estimated temperature of the production SMA element 22A during the test cycle period. For example, the tool controller 30 may define the estimated strain, and the estimated temperature as inputs into the stress predicting grid 31, and get the stress of the production SMA element 22A as the output from the stress predicting grid 31. For example, referring to FIG. 8, a temperature value 156 and a strain value 158 intersect at point 160 on the plane defined by the first horizontal axis 150 and the second horizontal axis 152. Moving along line 162, which is parallel to the vertical axis 154, line 162 intersects the grid 31 of valid SMA states at point 164. Moving along line 166, which is parallel to the plane defined by the first horizontal axis 150 and the second horizontal axis 152, line 166 intersects the vertical axis 154 at point 168. Point 168 correlates to the estimated stress in the production SMA element 22A.

Once the tool controller 30 has estimated the stress in the production SMA element 22A using the stress predicting grid 31, the tool controller 30 may compare the estimated stress in the production SMA element 22A to a desired stress value range. The desired stress value range may represent an allowable operating stress range for the production SMA element 22A. By comparing the estimated stress to the desired stress range, the tool controller 30 may determine if the estimated stress in the production SMA element 22A during the test cycle period is within the desired stress value range, or is outside the desired stress value range. If the estimated stress of the production SMA element 22A is within the desired stress value range, then the tool controller 30 may signal or otherwise indicate that the production SMA element 22A is operating properly, or is within allowable parameters. If the estimates stress of the production SMA element 22A is not within the desired stress value range, then the tool controller 30 may signal or otherwise indicate that the production SMA element 22A is not operating properly, or is not within allowable parameters.

Figure 9:
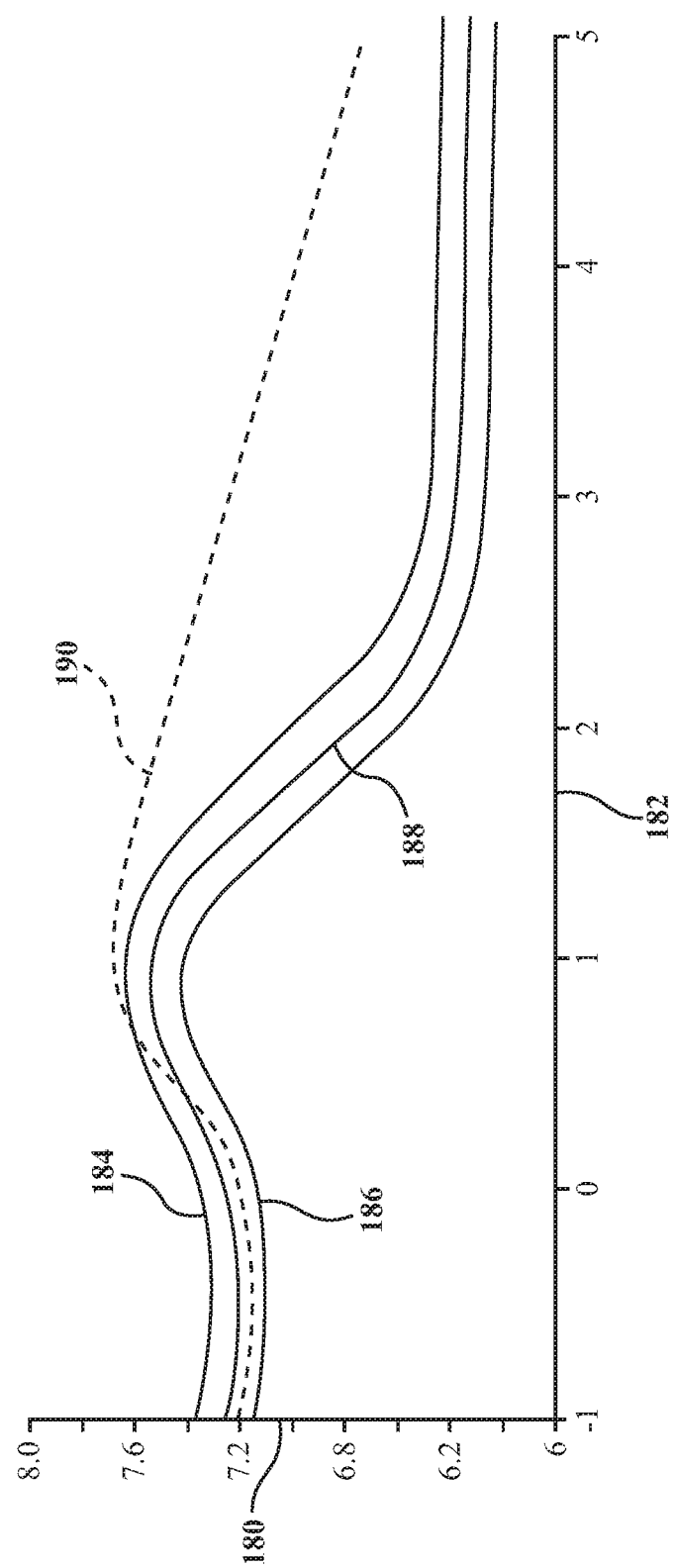
FIG. 9 is a graph of resistance vs. time of the production SMA element during a test cycle.

Alternatively, an allowable resistance profile for the production SMA element 22A may be developed from the calibration data obtained from testing the sample SMA element 22B. Referring to FIG. 9, the allowable resistance profile provides an allowable range of resistance values for the production SMA element 22A during the test cycle period. Within FIG. 9, resistance in ohms is shown on a vertical axis 180, and time in seconds is shown on a horizontal axis 182. An upper limit of the allowable resistance profile is shown at line 184, and a lower limit of the allowable resistance profile is shown at line 186. If the measured or calculated resistance of the production SMA element 22A during the test cycle period falls or lies within the range of resistance values, such as shown by line 188 in FIG. 9, for the entire test cycle period, then the tool controller 30 may determine that the production SMA element 22A is operating properly, and signal or otherwise indicate a "pass" value. Alternatively, if the measured or calculated resistance of the production SMA element 22A during the test cycle period falls or lies outside the range of resistance values, such as shown by line 190 in FIG. 9, for at least a portion of the test cycle period, then the tool controller 30 may determine that the production SMA element 22A is not operating properly, and signal otherwise indicate a "fail" value.

The detailed description and the drawings or figures are supportive and descriptive of the disclosure, but the scope of the disclosure is defined solely by the claims. While some of the best modes and other embodiments for carrying out the claimed teachings have been described in detail, various alternative designs and embodiments exist for practicing the disclosure defined in the appended claims.

The invention claimed is:

1. A method of testing a production Shape Memory Alloy (SMA) element, the method comprising:
   providing a stress predicting grid relating stress, strain, and temperature for the production SMA element;
   connecting a validation tool to the production SMA element;
   applying an electrical current to the production SMA element over a test cycle period;
   measuring a resistance of the production SMA element during the test cycle period, while the electrical current is being applied;
   correlating the measured resistance of the production SMA element during the test cycle period to an estimated strain value of the production SMA element during the test cycle period; and
   estimating a stress in the production SMA element during the test cycle period from the stress predicting grid using the estimated strain value during the test cycle period.

2. The method set forth in claim 1, further comprising estimating a temperature of the production SMA element during the test cycle period.

3. The method set forth in claim 2, wherein estimating the stress in the production SMA element during the test cycle period is further defined as estimating the stress in the production SMA element during the test cycle period from the stress predicting grid using the estimated strain value during the test cycle period and the estimated temperature of the production SMA element during the test cycle period.

4. The method set forth in claim 1, wherein providing the stress predicting grid includes testing a sample SMA element with a calibration rig, wherein the calibration rig is operable to apply a pre-determined force to the sample SMA element, while a current is applied to the sample SMA element during a calibration cycle period, and measure a resulting displacement of the sample SMA element during the calibration cycle period.

5. The method set forth in claim 4, wherein testing the sample SMA element includes conducting multiple tests of the sample SMA element, with each of the multiple tests using a different pre-determined force.

6. The method set forth in claim 4, wherein testing the sample SMA element includes measuring an ambient air temperature adjacent the sample SMA element, during the calibration cycle period.

7. The method set forth in claim 4, further comprising calculating a strain in the sample SMA element during the calibration cycle period, from the measured displacement of the sample SMA element during the calibration cycle period.

8. The method set forth in claim 7, wherein testing the sample SMA element includes measuring a resistance of the sample SMA element during the calibration cycle period.

9. The method set forth in claim 8, further comprising calculating a resistivity of the sample SMA element during the calibration cycle period.

10. The method set forth in claim 9, further comprising developing a relationship between resistance, strain, and temperature in the sample SMA element.

11. The method set forth in claim 10, wherein correlating the measured resistance of the production SMA element during the test cycle period to an estimated strain value in the production SMA element during the test cycle period includes referencing the relationship between resistance, strain, and temperature in the sample SMA element to correlate the measured resistance of the production SMA element to the estimated strain value of the production SMA element during the test cycle period.

12. The method set forth in claim 10, wherein providing the relationship between resistance, strain, and temperature in the sample SMA element includes calculating resistivity of the sample SMA element using the equation:

$$\rho = \xi(\alpha_{M1}T + \alpha_{M2}T^2 + \lambda_M) + (1-\xi)(\alpha_A T + \lambda_M) \quad 1)$$

wherein $\rho$ is the resistivity of the sample SMA element, $\xi$ is the martensite phase fraction of the sample SMA element, $\alpha_{M1}$ is the linear portion of the slope of a line relating resistance and temperature for pure martensite of the sample SMA element, $\alpha_{M2}$ is quadratic portion of the line relating resistance and temperature for pure martensite of the sample SMA element, T is the estimated temperature of the sample SMA element, $\lambda_M$ is the resistance offset of pure martensite at a reference temperature, and $\alpha_A$ is the slope of a line relating resistance and temperature for pure austenite of the sample SMA element.

13. The method set forth in claim 7, further comprising calculating a stress in the sample SMA element during the calibration cycle period from the pre-determined force applied to the sample SMA element during the calibration cycle period.

14. The method set forth in claim 13, further comprising estimating a temperature of the sample SMA element during the calibration cycle period, using a heat heat transfer model that relates electrical energy applied to the sample SMA element to a temperature of the sample SMA element.

15. The method set forth in claim 14, wherein providing the stress predicting grid includes developing the stress predicting grid using the calculated strain in the sample SMA element, the calculated stress in the sample SMA element, and the estimated temperature of the sample SMA element.

16. The method set forth in claim 1, further comprising comparing the estimated stress in the production SMA element to a desired stress value range to determine if the estimated stress in the production SMA element during the test cycle period is within the desired stress value range, or is outside the desired stress value range.

17. The method set forth in claim 1, further comprising developing an allowable resistance profile for the production SMA element, which provides an allowable resistance range of resistance values for the production SMA element during the test cycle period.

18. The method set forth in claim 17, further comprising signaling a pass value when the measured resistance of the production SMA element during the test cycle period is within the allowable resistance profile, and signaling a fail value when the measured resistance of the production SMA element during the test cycle period is outside the allowable resistance profile.

19. A validation tool for testing a Shape Memory Alloy (SMA) element, the validation tool comprising:
a resistance sensor for sensing a resistance of the SMA element;
a data acquisition unit in communication with the resistance sensor;
a thermocouple in communication with the data acquisition unit, and operable to sense an ambient air temperature adjacent the SMA element; and
a tool controller in communication with the data acquisition unit, the tool controller including a processor and non-transitory memory on which is recorded a test algorithm, wherein the processor is operable to execute the test algorithm to:
apply a constant electrical current to the SMA element for a test cycle;
measure a resistance in the SMA element during the test cycle;
estimate a strain in the SMA element, based on the measured resistance in the SMA element during the test cycle;
estimate a temperature of the SMA element during the test cycle; and
estimate stress in the SMA element during the test cycle, with a stress predicting grid that correlates the estimated strain in the SMA element during the test cycle and the estimated temperature of the SMA element during the test cycle, to the estimated stress in the SMA element during the test cycle.

* * * * *